United States Patent
Peng

(10) Patent No.: US 11,786,201 B1
(45) Date of Patent: Oct. 17, 2023

(54) METHOD AND SYSTEM FOR MATERIAL DECOMPOSITION IN DUAL- OR MULTIPLE-ENERGY X-RAY BASED IMAGING

(71) Applicant: StraxCorp Pty. Ltd, Melbourne (AU)

(72) Inventor: Yu Peng, Melbourne (AU)

(73) Assignee: CURVEBEAM AI LIMITED, Melbourne (AU)

(*) Notice: Subject to any disclaimer, the term of this patent is extended or adjusted under 35 U.S.C. 154(b) by 0 days.

(21) Appl. No.: 17/839,707

(22) Filed: Jun. 14, 2022

(51) Int. Cl.
*A61B 6/00* (2006.01)
*A61B 6/03* (2006.01)

(52) U.S. Cl.
CPC .............. *A61B 6/482* (2013.01); *A61B 6/032* (2013.01); *A61B 6/4241* (2013.01)

(58) Field of Classification Search
CPC ........ A61B 6/482; A61B 6/032; A61B 6/4241
See application file for complete search history.

(56) References Cited

U.S. PATENT DOCUMENTS

| | | | | |
|---|---|---|---|---|
| 6,891,918 | B2* | 5/2005 | Drummond | A61B 6/032 600/431 |
| 7,031,426 | B2* | 4/2006 | Iatrou | A61B 6/482 378/18 |
| 9,430,842 | B1* | 8/2016 | Hayat | G06T 7/13 |
| 2018/0114314 | A1* | 4/2018 | Butler | G06T 5/20 |
| 2019/0290226 | A1* | 9/2019 | Gotman | A61B 6/482 |
| 2020/0043204 | A1 | 2/2020 | Fu et al. | |
| 2020/0196973 | A1 | 6/2020 | Zhou et al. | |
| 2020/0281543 | A1* | 9/2020 | Sahbaee Bagherzadeh | G06T 11/005 |
| 2021/0012463 | A1* | 1/2021 | Ramani | G06T 11/005 |

OTHER PUBLICATIONS

Chen et al., "CrossViT: Cross-Attention Multi-Scale Vision Transformer for Image Classification", Aug. 22, 2021, (12 pages).
Australian Examination Report No. 1 for Australian App. No. 2022204142, dated Aug. 2, 2022 (8 pages).
(Continued)

*Primary Examiner* — Molly Wilburn
(74) *Attorney, Agent, or Firm* — NIXON PEABODY LLP; Jeffrey L. Costellia

(57) ABSTRACT

A method and system for generating material decomposition images from plural-energy x-ray based imaging, the method comprising: modelling spatial relationships and spectral relationships among the plurality of images by learning features from the plurality of images in combination and one or more of the plurality of images individually with a deep learning neural network; generating one or more basis material images employing the spatial relationships and the spectral relationships; and generating one or more material specific or material decomposition images from the basis material images. The neural network has an encoder-decoder structure and includes a plurality of encoder branches; each of one or more of the plurality of encoder branches encodes two or more images of the plurality of images in combination; and each of one or more of the plurality of encoder branches encodes a respective individual image of the plurality of images.

20 Claims, 8 Drawing Sheets

(56) References Cited

OTHER PUBLICATIONS

International Search Report for Application No. PCT/AU2023/050517, dated Jun. 28, 2023 (5 pages).
Wu et al. "Consensus Neural Network for Medical Imaging Denoising with Only Noisy Training Samples", arXiV e-prints, (2019), arXiV-1906, Published Jun. 9, 2019, pp. 1-9.
Fang et al., "Iterative Material Decomposition for Spectral CT using Self-Supervised Noise2Nosise Prior", Physics in Medicine & Biology 66, (2021), 155013, Published Jul. 27, 2021, (17 pages).

* cited by examiner

METHOD AND SYSTEM FOR MATERIAL DECOMPOSITION IN DUAL- OR MULTIPLE-ENERGY X-RAY BASED IMAGING

FIELD OF THE INVENTION

The present invention relates to a deep learning method and system for material decomposition in plural—(i.e. dual- or multiple-) energy x-ray based imaging, including cold cathode x-ray CT or radiography, dual-energy CT or radiography, multi-energy CT or radiography, and photon-counting CT or radiography.

BACKGROUND

Since its introduction, CT has been used widely in the medical diagnostic and therapeutic areas. Although CT technology has undergone numerous advances, its basic principle has been the same: it uses a rotating x-ray tube and a row of detectors placed in the gantry to measure x-ray attenuations by different tissues inside the body. Compared with other image modalities, CT has many advantages: fast scanning speed, high spatial resolution, and broad availability. Millions of CT examinations are performed annually, making CT one of the most important and widespread imaging modalities used for patient care.

Despite its remarkable success, CT technology has several limitations. One of the most substantial limitations is its low contrast resolution. It cannot reliably differentiate between the material with low inherent contrast, such as pathologic and healthy tissues. The low contrast resolution is due to the slight difference in x-ray attenuation between different tissues. For example, it is difficult to reliably assess noncalcified plaques because the differences in attenuation between lipid-rich and lipid-poor noncalcified plaques are minimal. It is also challenging to segment soft tissue structures such as cartilage from the keen CT scans due to the low contrast of the cartilage from the surrounding soft tissues.

In clinical imaging, contrast agents enhance the material contrast in CT scans. The contrast agents absorb external x-rays, resulting in decreased exposure on the x-ray detector. Contrast agents such as iodinated agents could cause kidney damage and trigger allergic reactions.

In the conventional CT, the attenuation value of each voxel is the combined attenuation of multiple materials. Dual-energy CT uses two separate x-ray photon energy spectra rather than the single energy technology used in conventional CT. It allows the interrogation of materials that have different attenuation properties at different energies. However, due to the limit of two energy bins, the tissue discrimination is still suboptimal. With more than two energies and narrow energy ranges, multi-energy CT can concurrently identify multiple materials with increased accuracy.

Photon-counting CT is an emerging technology that has been shown tremendous progress in the last decade. With photon-counting detectors, each photon of the incident x-rays hits the detector element and generates an electrical pulse with a height proportional to the energy deposited by the individual photon. Photon-counting CT inherently allows dual-energy or multi-energy acquisitions at a single source, a single tube, a single acquisition, a single detector, and a single filter. Moreover, the user-defined energy threshold selection allows the choice of suitable energy thresholds tailored to the specific energy diagnostic task. This task-driven energy-threshold selection helps resolve different tissue types with optimal imaging settings to achieve the best image quality or lowest radiation dose.

With either multi-energy CT or photon counting CT, the basic principle of material decomposition is the same: it determines the full energy dependence of the attenuation curve in every voxel of a scan. The assumption is that any human tissue is approximately equivalent to a combination of two or more basis materials, as far as x-ray attenuation properties are concerned. Although any materials can be employed as basis materials, water, calcium, iodine or fat are usually used as the basis materials. Consequently, material decomposition is also referred to as basis material decomposition. The general workflow is as follows. Using multi-energy CT or photon counting CT, the energy selective (or energy-specific) images are produced by the multi-energy bins. A set of basis material images is generated from the energy-selective images. Each basis material image represents the equivalent concentration of basis material for each voxel in the scan. The basis images can be used to obtain images of human tissues such as bone, muscle, and fat through a linear transformation of the basis images. To find the transformation formula for a piece of human tissue, the concentrations of each basis material is calculated.

Material decomposition methods have been developed. The simplest method is inversing the matrix that relates attenuation values to material concentrations. Other methods were also advanced, such as optimization with regularization. However, with the assumption of the type and numbers of basis materials, material decomposition is a non-linear ill-posed problem and inaccurate decomposition is a problem in current methods.

Recently, machine learning, especially deep learning methods, has shown promise in solving ill-posed problems such as image reconstruction, image resolution enhancement, and voice recognition. In this invention, a deep learning method and system is invented to present the mapping between the energy-selective images and material-specific images.

SUMMARY

It is an object of the present invention to provide a method of generating material decomposition images from plural-energy x-ray based imaging.

According to a first aspect of the invention, there is provided a method for generating material decomposition images from a plurality of images obtained with plural-energy x-ray based imaging, the plurality of images corresponding to respective energies of the plural-energy x-ray based imaging, the method comprising:

modelling spatial relationships and spectral relationships among the plurality of images by learning features from the plurality of images in combination and one or more of the plurality of images individually with a deep learning neural network;

generating one or more basis material images employing the spatial relationships and the spectral relationships; and generating one or more material specific or material decomposition images from the basis material images (such as through a linear transformation of the basis material images);

wherein the neural network has an encoder-decoder structure (e.g. comprising an encoder network and an decoder network) and includes a plurality of encoder branches;

each of one or more of the plurality of encoder branches encodes two or more images of the plurality of images in combination (e.g. together, concatenated or in series); and each of one or more of the plurality of encoder branches encodes a respective individual image of the plurality of images.

Spatial relationships and spectral relationships are respectively relationships between the spatial information (i.e. of the objects, materials and structures in the images) and spectral information (i.e. the different material attenuations arising from different photon energies).

It should be noted that the plurality of images obtained with plural-energy x-ray based imaging may be synthetic, in the sense that they may not have been obtained simultaneously or in a single scan, but instead compiled from a plurality of scans.

The one or more encoder branches that encode two or more images of the plurality of images in combination may receive the respective two or more images in combination, concatenated, etc.., or combine, concatenate, etc.., the respective two or more images before encoding them.

In an embodiment, each of two or more of the encoder branches encodes a respective different individual image of the plurality of images.

In some embodiments, a first encoder branch encodes a first combination of two or more images of the plurality of images and a second encoder branch encodes a second combination of two or more images of the plurality of images, wherein the first combination is different from the second combination (though the combinations may include common images).

The plural-energy x-ray based imaging may comprise, for example, cold cathode x-ray radiography, dual-energy radiography, multi-energy radiography, photon-counting radiography, cold cathode x-ray CT, dual-energy CT, multi-energy CT or photon-counting CT.

Advantageously, in some embodiments the encoder branches that encode a respective individual image encode in total all of the images that are encoded in total by the encoder branches that encode two or more images.

However, in some other embodiments, the encoder branches that encode a respective individual image receive in total fewer images (such as by omitting one or more low-energy images) than are encoded in total by the encoder branches that encode two or more images. This may be done, for example, to reduce computation time.

In still other embodiments, the encoder branches that encode a respective individual image encode in total more images than are encoded in total by the encoder branches that encode two or more images.

The encoder branches that encode a respective individual image may encode only images than are not encoded by any of the encoder branches that encode two or more images. However, more advantageously, the encoder branches that encode a respective individual image encode in total at least one image than is also encoded by at least one of the encoder branches that encode two or more images.

In one implementation of the invention, the combination of all of the images (referred to as the 'energy images', as each corresponds to a respective x-ray energy bin or energy threshold) is used as input to a first encoder branch, and each of the individual energy images is used as the input to a respective one of a plurality of further branches. However, in some implementations, not all of the energy images are used as input to the first encoder branch and/or as inputs to respective further branches: some energy images may be omitted. For example, if the targeted basis material images (i.e. those of interest) relate to soft tissues only, high energy images may be omitted. On the other hand, high energy images are useful for differentiating hard materials such as bone, so in implementations in which the basis material images of interest relate to hard tissues, low energy images may be omitted.

It may also be advantageous (such as to reduce computing overhead) in these or other implementations to omit one or more energy images so that the neural network is smaller and simpler, with fewer encoder branches.

Hence, in an embodiment, each of the one or more of the encoder branches respectively encodes an individual image corresponding to a low x-ray energy, and the material decomposition images correspond to one or more soft tissues. In an embodiment, each of the one or more of the encoder branches respectively encodes an individual image corresponding to a high x-ray energy, and the material decomposition images correspond to one or more hard tissues.

It is appreciated that 'low' and 'high' may be viewed as relative terms, but the appropriate low- or high-energy subset of the entire set of energy images can be readily selected by simple experimentation, balancing the quality of the results (measured in terms of resolution or completeness of material decomposition) against computing time or computing overhead.

However, in one example, the low x-ray energy images (of n-images obtained with plural-energy x-ray based imaging) comprise the n-1, n-2 or n-3 images of lowest energy. In another example, the low x-ray energy images comprise the one or two images of lowest energy.

In one example, the high x-ray energy images comprise the n-1, n-2 or n-3 images of highest energy. In another example, the high x-ray energy images comprise the one or two images of highest energy.

In an embodiment, the deep learning neural network is a trained neural network, trained with real or simulated training images obtained with real or simulated plural-energy x-ray based imaging and with basis material images. For example, the basis material images may comprise any one or more (i) HA (hydroxyapatite) images, (ii) calcium images, (iii) water images, (vi) fat images, (v) iodine images, and (vi) muscle images.

In certain embodiments, the method comprises generating any one or more of (i) a bone marrow decomposition image, (ii) a knee cartilage decomposition image, (iii) an iodine contrast decomposition image, (iv) a tumor decomposition image, (v) a muscle and fat decomposition image, (vi) a metal artefact reduction image, and (vii) a beam hardening reduction image.

The method may comprise:
  generating one or more bone marrow images, and diagnosing, identifying or monitoring bone marrow related disease using the one or more bone marrow images;
  generating one or more knee cartilage images, and diagnosing, identifying or monitoring osteoarthritis or rheumatoid arthritis using the one or more bone marrow images;
  generating one or more iodine contrast image, and diagnosing, identifying or monitoring a tumor; and/or
  generating one or more muscle images, and diagnosing, identifying or monitoring sarcopenia.

The method may comprise:
  generating any one or more (a) bone marrow images, (b) knee cartilage images, (c) iodine contrast images, and (d) muscle images;

generating one or more metal artefact images and/or one or more beam hardening reduction images; and improving image quality of the bone marrow, knee cartilage, iodine contrast and/or muscle images using the metal artefact and/or beam hardening reduction images.

The method may include training or retraining deep learning models using the neural network.

The method may include combining features extracted by the one or more encoder branches that encode two or more images in combination and features extracted by the one or more encoder branches that encode respective individual images using a concatenation layer at the end of or after an encoder network of the neural network.

In other embodiments, the method includes combining features extracted by the one or more encoder branches that encode two or more images in combination and features extracted by the one or more encoder branches that encode respective individual images using one or more concatenation operations at plural levels of an encoder network of the neural network.

In still other embodiments, the method includes combining features extracted by the one or more encoder branches that encode two or more images in combination and features extracted by the one or more encoder branches that encode respective individual images using concatenation operations that connect an encoder network of the neural network and a decoder network of the neural network at multiple levels.

In yet other embodiments, the method includes combining features extracted by the one or more encoder branches that encode two or more images in combination and features extracted by the one or more encoder branches that encode respective individual images, but an encoder network of the neural network and an decoder network of the neural network are not connected at multiple levels.

According to this aspect, there is also provided a material decomposition image, generated according to the method of this aspect (including any of its embodiments) from a plurality of images obtained with plural-energy x-ray based imaging.

According to a second aspect of the invention, there is provided a system for generating material decomposition images from a plurality of images obtained with plural-energy x-ray based imaging, the plurality of images corresponding to respective energies of the plural-energy x-ray based imaging, the system comprising:

the neural network has an encoder-decoder structure (e.g. comprising an encoder network and an decoder network) and includes a plurality of encoder branches;

wherein each of one or more of the plurality of encoder branches is configured to encode two or more images of the plurality of images in combination (e.g. together, concatenated or in series); and each of one or more of the plurality of encoder branches is configured to encode a respective individual image of the plurality of images as input;

the neural network is configured to model spatial relationships and spectral relationships among the plurality of images by learning features from the plurality of images in combination and one or more of the plurality of images individually with a deep learning neural network, and to generate one or more basis material images employing the spatial relationships and the spectral relationships; and the system is configured to generate one or more material specific or material decomposition images from the basis material images.

The one or more encoder branches that encode two or more images of the plurality of images in combination may receive the respective two or more images in combination, concatenated, etc., or combine, concatenate, etc., the respective two or more images before encoding them.

In an embodiment, each of two or more of the encoder branches is configured to encode a respective different image of the plurality of images.

In some embodiments, a first encoder branch is configured to encode a first combination of two or more images of the plurality of images as input and a second encoder branch is configured to encode a second combination of two or more images of the plurality of images as input, wherein the first combination is different from the second combination (though the combinations may include common images).

The plural-energy x-ray based imaging may comprise cold cathode x-ray radiography, dual-energy radiography, multi-energy radiography, photon-counting radiography, cold cathode x-ray CT, dual-energy CT, multi-energy CT or photon-counting CT.

Advantageously, in some embodiments the encoder branches configured to encode a respective individual image receive in total all of the images that are encoded in total by the encoder branches configured to encode two or more images.

However, in other embodiments, the encoder branches that encode a respective individual image are configured to encode in total fewer images (such as by omitting one or more low-energy images) than are encoded in total by the encoder branches that encode two or more images (such as to reduce computation time).

In still other embodiments, the encoder branches that encode a respective individual image are configured to encode in total more images than are encoded in total by the encoder branches that encode two or more images.

The encoder branches that encode a respective individual image may encode only images than are not encoded by any of the encoder branches that encode two or more images. However, more advantageously, the encoder branches that encode a respective individual image encode in total at least one image than is also encoded by at least one of the encoder branches that encode two or more images.

The deep learning neural network may be a trained neural network, trained with real or simulated training images obtained with real or simulated plural-energy x-ray based imaging and with basis material images. For example, the basis material images may comprise any one or more (i) HA (hydroxyapatite) images, (ii) calcium images, (iii) water images, (vi) fat images, (v) iodine images, and (iv) muscle images.

The system may be configured to generate any one or more of (i) a bone marrow decomposition image, (ii) a knee cartilage decomposition image, (iii) an iodine contrast decomposition image, (iv) a tumor decomposition image, (v) a muscle and fat decomposition image, (vi) a metal artefact reduction image, and (vii) a beam hardening reduction image.

In an embodiment, the system is configured:

to generate one or more bone marrow images, and to diagnose, identify or monitor bone marrow related disease using the one or more bone marrow images;

to generate one or more knee cartilage images, and to diagnose, identify or monitor osteoarthritis or rheumatoid arthritis using the one or more bone marrow images;

to generate one or more iodine contrast image, and to diagnose, identify or monitor a tumor; and/or to generate one or more muscle images, and to diagnose, identify or monitor sarcopenia. The system may be configured to:

generate any one or more (a) bone marrow images, (b) knee cartilage images, (c) iodine contrast images, and (d) muscle images;

generate one or more metal artefact images and/or one or more beam hardening reduction images; and improve image quality of the bone marrow, knee cartilage, iodine contrast and/or muscle images using the metal artefact and/or beam hardening reduction images.

The system may include deep learning model trainer configured to train or retrain deep learning models using the neural network.

The system may be configured to combine features extracted by the one or more encoder branches that encode two or more images in combination and features extracted by the one or more encoder branches that encode respective individual images using a concatenation layer at the end of or after an encoder network of the neural network.

In other embodiments, the system may be configured to combine features extracted by the one or more encoder branches that encode two or more images in combination and features extracted by the one or more encoder branches that encode respective individual images using one or more concatenation operations at plural levels of an encoder network of the neural network.

In still other embodiments, the system may be configured to combine features extracted by the one or more encoder branches that encode two or more images in combination and features extracted by the one or more encoder branches that encode respective individual images using concatenation operations that connect an encoder network of the neural network and an decoder network of the neural network at multiple levels.

In yet other embodiments, the system may be configured to combine features extracted by the one or more encoder branches that encode two or more images in combination and features extracted by the one or more encoder branches that encode respective individual images, wherein an encoder network of the neural network and an decoder network of the neural network are not connected at multiple levels.

According to a third aspect of the invention, there is provided a computer program comprising program code configured, when executed by one of more computing devices, to implemented the method of the first aspect (and any of its embodiments). According to this aspect, there is also provided a computer-readable medium (which may be non-transient), comprising such a computer program.

It should be noted that any of the various individual features of each of the above aspects of the invention, and any of the various individual features of the embodiments described herein, including in the claims, can be combined as suitable and desired.

DRAWINGS

In order that the invention may be more clearly ascertained, embodiments will now be described by way of example with reference to the following drawing, in which.

DETAILED DESCRIPTION

Figure 1:
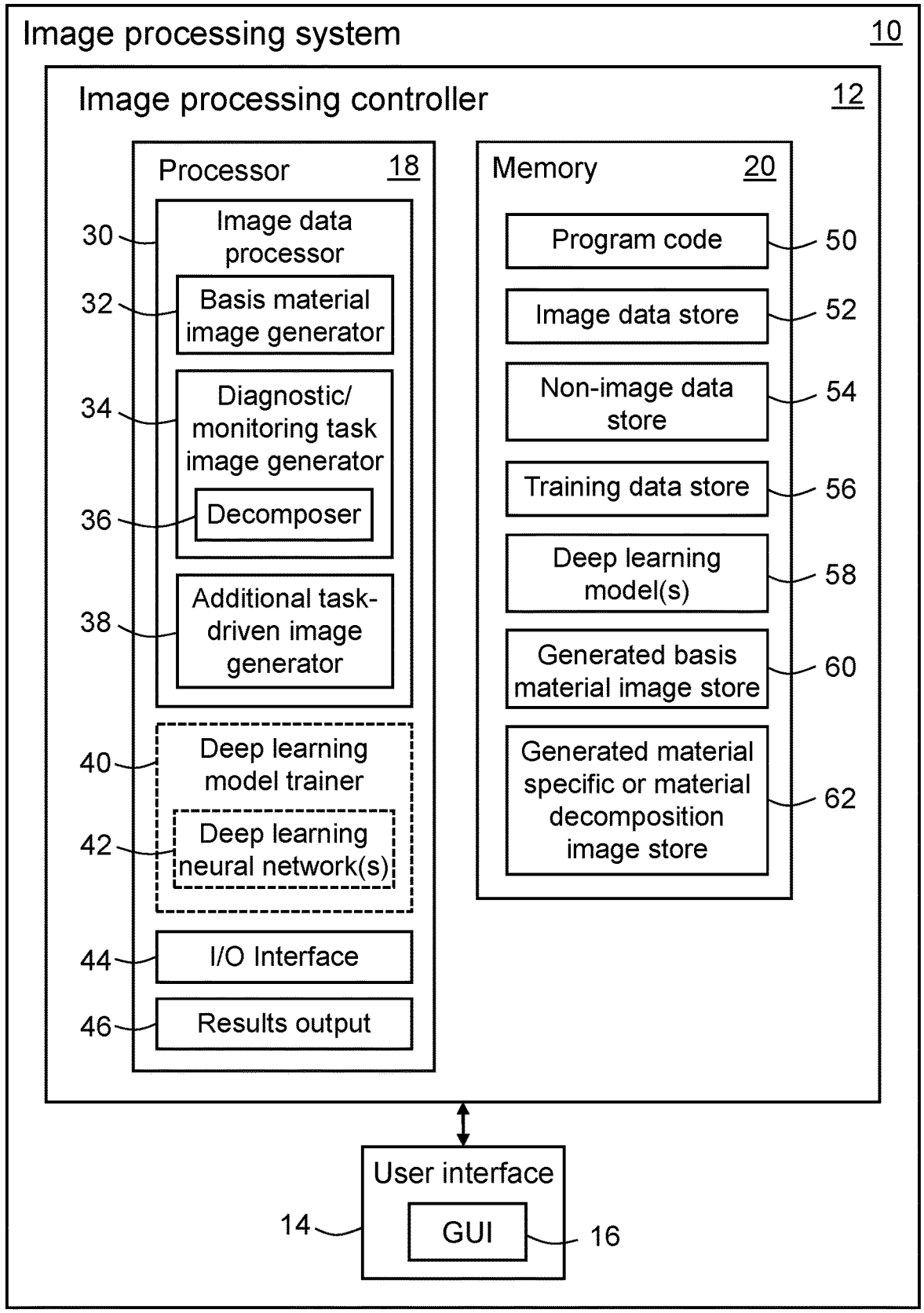
FIG. 1 is a schematic view of an image processing system according to an embodiment of the present invention.

FIG. 1 is a schematic view of an image processing system 10 (of application in particular for processing medical images) according to an embodiment of the present invention.

System 10 includes an image processing controller 12 and a user interface 14 (including a GUI 16). User interface 14 includes one or more displays (on one or more of which may be generated GUI 16), a keyboard and a mouse, and optionally a printer.

Image processing controller 12 includes at least one processor 18 and a memory 20. Instructions and data to control operation of processor 18 are stored in memory 20.

System 10 may be implemented as, for example, a combination of software and hardware on a computer (such as a server, personal computer or mobile computing device) or as a dedicated image processing system. System may optionally be distributed; for example, some or all of the components of memory 20 may be located remotely from processor 18; user interface 14 may be located remotely from memory 20 and/or from processor 18 and, indeed, may comprise a web browser or a mobile device application.

Memory 20 is in data communication with processor 18, and typically comprises both volatile and non-volatile memory (and may include more than one of type of memory), including RAM (Random Access Memory), ROM and one or more mass storage devices.

As is discussed in greater detail below, processor 18 includes an image data processor 30, which includes a basis material image generator 32, a diagnostic/monitoring task image generator 34 (including a decomposer 36), and an additional task-driven image generator 38. Processor 18 further includes a deep learning model trainer 40 (which includes one or more deep learning neural networks 42), an I/O interface 44 and an output in the form of a results output 46. Deep learning model trainer 40 may be omitted in some implementations of this and other embodiments, as it is required only if system 10 is itself to train deep learning model(s) 58, rather than access one or more suitable deep learning models from an external source.

Memory 20 includes program code 50, image data store 52, non-image data store 54, training data store 56, trained deep learning model(s) 58, generated basis material image store 60 and generated material specific or material decomposition image store 62. Image processing controller is implemented, at least in part, by processor 18 executing program code 50 from memory 20.

In broad terms, the I/O interface 44 is configured to read or receive image data (such as in DICOM format) and non-image data, pertaining to—for example—subjects or patients, into image data store 52 and non-image data store 54 of memory 20, respectively, for processing. The non-image data stored in non-image data store 54 comprises broad information such as energies, desired materials and desired tasks, and is accessible by image generators 32, 34, 36 for use in image generation.

Basis material image generator 32 of image data processor 12 generates one or more sets of basis material images with one or more machine learning models (drawn from deep learning model(s) 58). Diagnostic/monitoring task image generator 34 uses decomposer 36 to generate one or more sets of material specific or material decomposition images (suitable for, for example, diagnostic or monitoring tasks) using the basis material images, and additional task-driven image generator 38 generates at least one further set of images (such as beam hardening or metal artefact reduced images). I/O interface 44 outputs the results of the processing to, for example, results output 46 and/or to GUI 16.

System 10 employs one or more deep learning models to accurately and reproducibly generate the basis material images. The basis material images are then used for generating images of different tissues and materials, especially of low contrast tissues and materials, which can in turn be used in pathology or disease identification and monitoring (such as of disease progression). For example, cartilage segment images from the knee scan may be used for osteoarthritis or rheumatoid arthritis diagnosis and/or monitoring; bone marrow segment images from musculoskeletal scans may be used for related diseases diagnosis and monitoring of associated diseases or pathologies; pathological and normal tissue images from a scan of a patient may be used for diagnosis and monitoring of a tumor; simultaneous material decomposition of multiple contrast agents from a CT scan may be used for the diagnosis or identification, and staging, of renal abnormalities; muscle extracted images may be used for sarcopenia diagnosis and/or monitoring.

System 10 can also generate images for other tasks (using additional task-driven image generator 38). For example, system 10 can generate beam-hardening or metal artefact reduced images based on the aforementioned basis material images for better image quality. Beam hardening or metal artefact effects occur when a polychromatic x-ray beam passes through an object, resulting in selective attenuation—principally affecting lower energy photons. As a result, higher energy photons solely or excessively contribute to the beam, thereby increasing the mean beam energy—an effect known as 'beam hardening.' As the full energy-dependent attenuation is considered in material decomposition, it is thus desirable that the decomposed images be free of beam-hardening and metal artefact effects.

Thus, referring to FIG. 1, system 10 is configured to receive two types of data pertaining to a subject or patient: image data and non-image data. The image data is on the form of plural-energy images based on or derived from x-ray imaging, such as may be generated in cold cathode x-ray radiography, dual-energy CT, multi-energy CT or photon-counting CT. The non-image data includes information about the plural-energy images, such as the energies at which the plural-energy images were generated, information about the desired basis material images, such as the type and number of the basis material images, and information about the desired analysis or analyses, such as disease diagnosis/identification/monitoring or additional tasks (e.g., beam hardening or metal artefact reduction). System 10 stores image data and non-image data in the image data store 52 and non-image data store 54, respectively.

As mentioned above, image data processor 30 includes three components: basis material image generator 32, diagnostic/monitoring task image generator 34, and additional task-driven image generator 38. The image data and non-image data are received by image data processor 30 from memory 20. Based on the plural-energy images and the basis material in the non-image data, image data processor 30 selects one or more suitable deep learning models 58 to generate one or more sets of basis material images. Based on the task information, image data processor 30 generates images (e.g., human tissues, contrast agents images) for disease diagnosis/identification and/or monitoring, and images (e.g. beam hardening and metal artefact reduced images) for better image quality.

Deep learning model trainer 40 pre-trains deep learning models 58 using training data (from training data store 56) that includes labels or annotations that constitute the ground truth for machine learning. The training data is prepared so as to be suitable for training a deep-learning model for generating basis material images from the plural-energy images. The training data consists of both known plural-energy images and known basis material images. The labels indicate the energy bin of each energy image (that is, an image corresponding to a particular energy threshold or bin) and the material information (e.g., material name and material density) of the basis material images. The training data can be in the form of real clinical data, real phantom data, simulated data, or a mixture of two or more of these.

As mentioned above, deep learning model trainer 40 is configured to train one or more deep learning models (and to retrain or update train deep learning models) using neural network 42 and the training data, but in other embodiments machine learning model trainers may be configured or used only to retrain or update (i.e., re-train) one or more existing deep learning models.

Image data processor 30 selects one or more suitable deep learning models from deep learning model(s) 58, based on the plural-energy images and the targeted basis material(s) (as identified in the non-image data). Basis material image generator 32 generates images of the targeted basis material. Diagnostic/monitoring task image generator 34 generates images according to the information concerning diagnosis/identification and/or monitoring tasks (as also identified in the non-image data), from the generated basis material images. Optionally, additional task-driven image generator 38 generates images according to the information of the additional tasks (as also identified in the non-image data), from the generated basis material images.

The basis material images, diagnostic/monitoring images, and/or additional task-driven images are outputted to user interface 14 via results output 46 and I/O interface 44.

Figure 2:
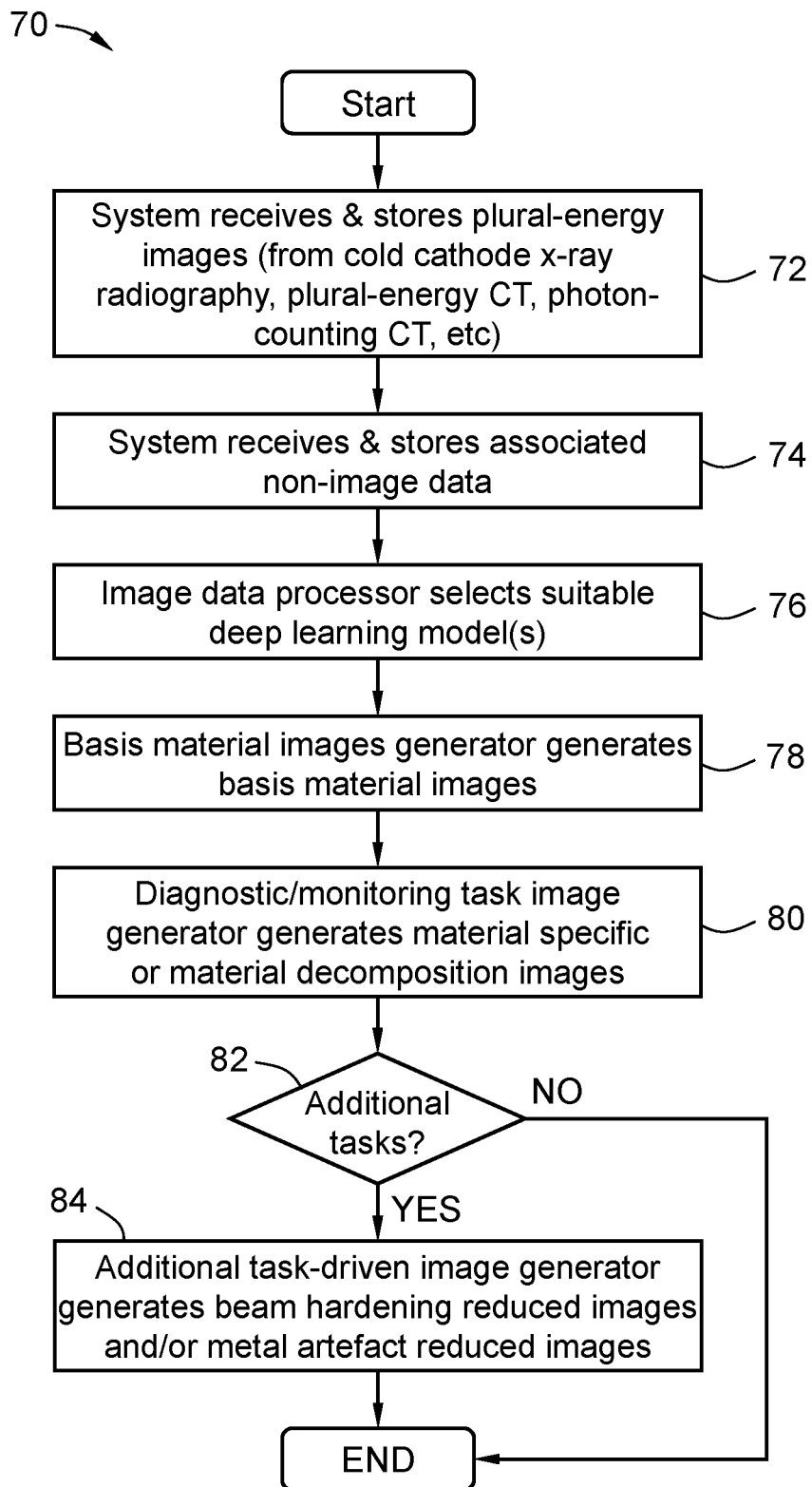
FIG. 2 is a schematic flow diagram of the general workflow of the system of FIG. 1.

FIG. 2 is a flow diagram 70 of the general workflow of system 10 of FIG. 1. Referring to FIG. 2, at step 72 system 10 receives plural-energy images (generated by, for example, dual-energy, multi-energy or photon-counting CT or radiography) and reads the images into image data store 52. At step 74, system 10 receives associated non-image data and reads that data into non-image data store 54.

Memory 20 is advantageously configured to allow high-speed access of data by system 10. For example, if system 10 is implemented as a combination of software and hardware on a computer, the images are desirably read into RAM of memory 20.

At step 76, image data processor 30 selects one or more suitable deep learning models from the trained deep learning model(s) 58. The deep learning model selection is based on the energy information characterizing the plural-energy images and the information concerning the targeted basis material, both contained in the non-image data. Any particular model is trained using the images of specific energies to generate a specific set of basis material images; hence, more than one suitable model may be trained and available. According to the energies and desired basic material specs, the corresponding model or models are is selected. If plural models are selected, they are used in parallel.

For example, one deep learning model may be selected for use with all loaded images for generating one set of basis material images. In another example, more than one deep learning model is chosen for use with all loaded images for generating several sets of basis material images. In another example, more than one deep learning model is selected to use with respective subsets of the loaded images, for generating one or more sets of basis material images.

The selected deep learning model or models include spatial relationships and spectral relationships learned from training data. At step 78, basis material images generator 32 generates the basis material images from the loaded subject or patient images in image data store 52 using the one or more selected deep learning models and these spatial and spectral relationships, and saves the generated basis material images in generated basis material image store 60.

At step 80, diagnostic/monitoring task image generator 34 uses the generated basis material images to decompose the original subject or patient images in image data store 52 and thereby generate material specific or material decomposition images of, in this example, specific, different (e.g. human) tissues, suitable for disease identification, diagnosis and/or monitoring, and saves these material specific or decomposition images in generated material specific or material decomposition image store 62.

At step 82, image data processor 30 determines whether—according to the associated non-image data 54 indicating the desired task(s)—additional task-driven image generator 38 is required to generate any images. If not, processing ends. If so, at step 84, additional task-driven image generator 38 generates the appropriate task-driven images, such as beam hardening reduced images and/or metal artefact reduced images. Processing then ends.

Figure 3A:
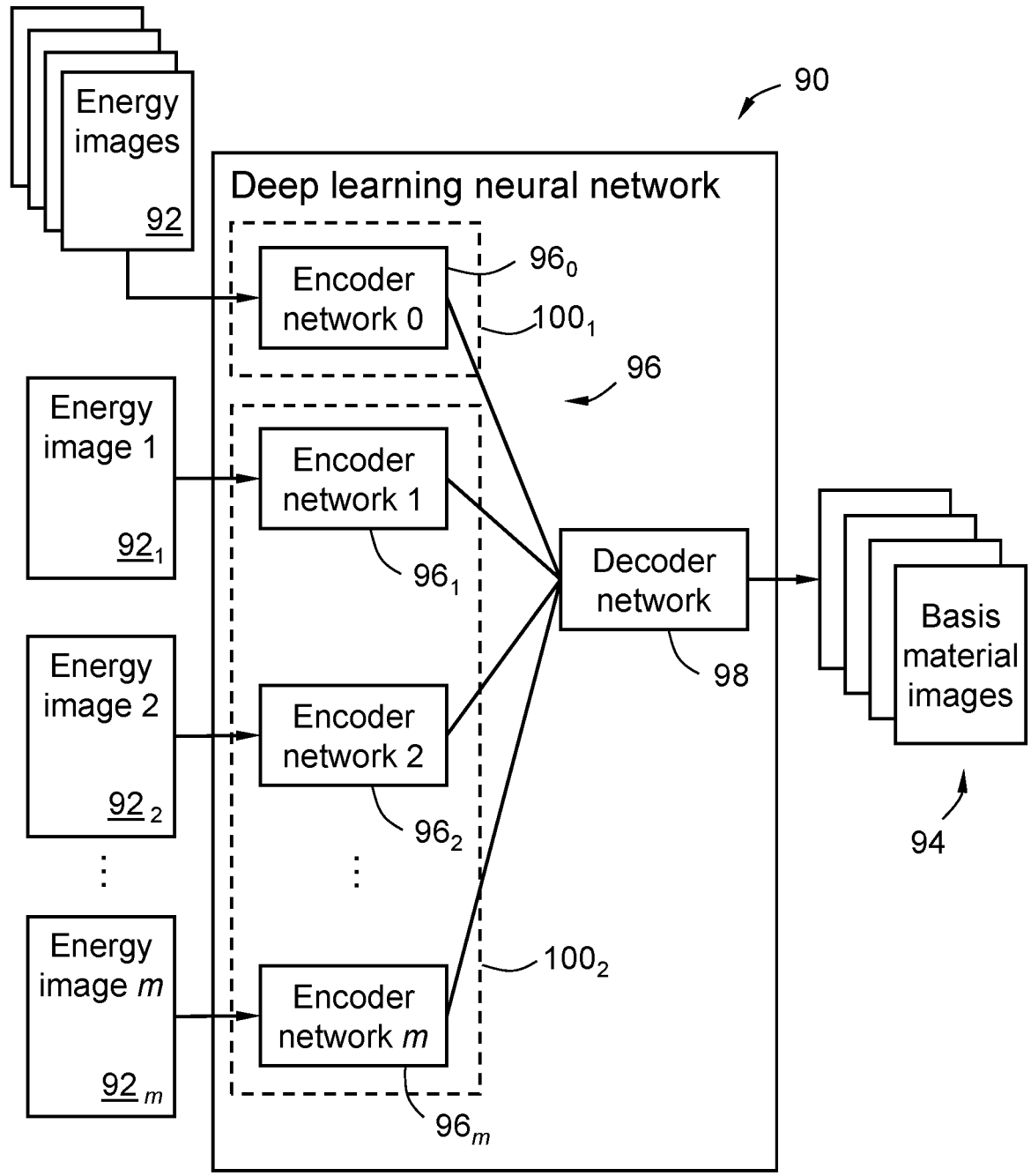
FIG. 3A is a schematic view of a deep learning neural network for generating material decomposition images from plural-energy images according to an embodiment of the present invention.

FIG. 3A is a schematic view of a deep learning neural network 90 (such as may be employed as neural network 42 of system 10), for generating material decomposition images from plural-energy images according to an embodiment of the present invention. Neural network 90 is shown with input in the form of n plural-energy x-ray based images 92 (where n≥2) and output in the form of basis material images 94. Neural network 90 is configured to generate basis material images 94 from the images 92. That is, the functional mapping between the input images 92 and output basis material images 94 is approximated by neural network 90, which is configured to predict material-specific images using the images 92 as input. Material decomposition images can then be generated from the generated basis material images 94.

Neural network 90 comprises an encoder network 96 and a decoder network 98. Encoder network 96 encrypts the structures of the input images (e.g. some or all of images 92) into a feature representation at multiple different levels. Decoder network 98 projects the discriminative feature representation learnt by encoder network 96 into the pixel/voxel space to get a dense classification. In one example, the encoding performed by encoder network 96 includes convolution operations and down-sampling operations; the decoding performed by decoder network 98 includes convolution operations and up-sampling operations. In another example, the encoding performed by encoder network 96 and/or the decoding performed by decoder network 98 include concatenation operations.

Encoder network 96 has a plural-branch structure, with a first set $100_1$ and a second set $100_2$ of encoder branches (each set having one or more encoder branches). Each of the branches of the first set $100_1$ of encoder branches encodes a plurality of images selected from images 92 (which may comprise all of images 92) in concatenated form. (It should be noted that this or these pluralities of images selected from images 92 for processing in concatenated form may be inputted either in concatenated form or non-concatenated form. In the latter case, the encoder network first concatenates the images.)

Each of the branches of the second set $100_2$ of encoder branches encodes an individual image selected from images 92. First set $100_1$ and second set $100_2$ may include, in total, the same or different numbers of images.

In the example of FIG. 3A, first set $100_1$ of encoder branches includes, in this example, one encoder network branch $96_0$ (comprising 'Encoder network 0') for encoding a plurality of images 92 (in this example all of images 92) in concatenated form. Second set $100_2$ of encoder branches includes a plurality m of encoder network branches $96_1$, $96_2$, ..., $96_m$ (comprising respectively 'Encoder network 1', 'Encoder network 2', ..., 'Encoder network m') for encoding each of the respective, individual input images $92_1$, $92_2$, ..., $92_m$, where m≤n. (Note that images 1, 2, ..., m need not be sequential or comprise the first m images of images 92. Also, encoder network branch $96_0$ may be configured to receive a plurality—but not all—of the images 92 in concatenated form.) The individual images $92_1$, $92_2$, ..., $92_m$ are generally of a conventional format for the respective imaging modality (e.g. DICOM, JPEG, TIFF or other imaging files), so are typically two- or three-dimensional images comprising pixels or voxels but, as they have an extra dimension indicative of energy threshold or bin, could be described as three- or four-dimensional. Likewise, the images 92 in concatenated or combined form have an extra dimension (indicative of energy threshold or bin), so may also be described as typically three- or four-dimensional.

Encoder network branch $96_0$ of the first set $100_1$ learns relationships among images 92 inputted into that branch and effectively combines them. Encoder network branch $96_0$ of the second set $100_2$ learn the features of each individual image $92_1$, $92_2$, ..., $92_m$ independently. The feature representations learned by the first set $100_1$ of network branches (viz. network branch $96_0$) and by the second set $100_2$ of network branches $96_1$, $96_2$, ..., $96_m$ are combined as the input of decoder network 98.

In one example, the features extracted by first set $100_1$ of encoder network branches $96_0$ and by second set $100_2$ of encoder network branches $96_1$, $96_2$, ..., $96_m$ are combined using a concatenation layer (not shown) at the end of or after encoder network 96. In another example (cf. the embodiment in FIG. 4), the features extracted from first set $100_1$ of branches and second set $100_2$ of branches are combined using one or more concatenation operations at the plural levels of encoder network 96.

In a further example (cf. the embodiment in FIG. 4), concatenation operations connect the encoder network 96 and decoder network 98 at multiple levels. In still another example, encoder network 96 is not connected to decoder network 98 at multiple levels.

As mentioned above, all of images 92 may be concatenated to form the input (or concatenated image) for input into first branch 96$_0$; alternatively, only some (but a plurality) of the input images 92$_1$, 92$_2$, . . . , 92$_m$ may be concatenated to form the input (or concatenated image) for input into first set 100$_1$ of encoder branches (viz. encoder branch 96$_0$). In one example, all of the images 92 are separately input into second set 100$_2$ of encoder branches but, in another example, some (i.e. one or more) of the images 92$_1$, 92$_2$, . . . , 92$_n$ might not be encoded by second set 100$_2$ of encoder branches. In addition, it should be noted that the images that are input into the first and second sets 100$_1$, 100$_2$ of encoder branches need not be the same, but are drawn from the same multi-energy images 92.

Thus, deep learning neural network 90, which may thus be described as a multi-branch encoder-decoder deep learning network, generates the basis material images 94 by inherently modelling spatial and spectral relationships among the plural-energy images 92.

Figure 3B:
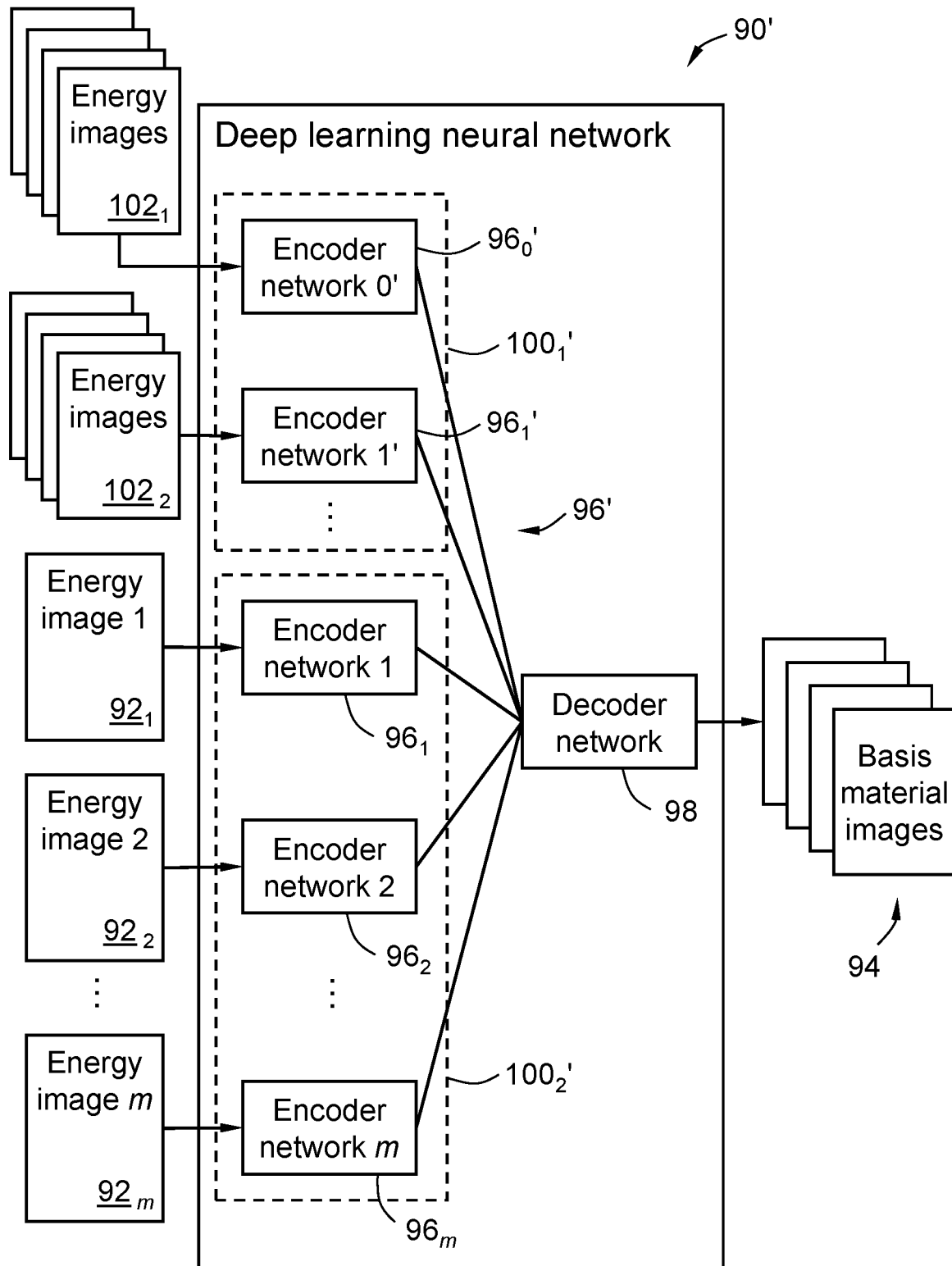
FIG. 3B is a schematic view of a deep learning neural network for generating material decomposition images from plural-energy images according to another embodiment of the present invention.

FIG. 3B is a schematic view of a deep learning neural network 90' (such as may be employed as neural network 42 of system 10), which is comparable to neural network 90 of FIG. 3A so like numerals have been used to indicate like features. Neural network 90' is thus also adapted for generating material decomposition images from plural-energy images according to an embodiment of the present invention.

Neural network 90' includes an encoder network 96' that includes first and second sets 100$_1$', 100$_2$' of encoder branches. Neural network 90' differs from neural network 90 of FIG. 3A in that the first set 100$_1$' of encoder branches of neural network 90' includes at least two encoder branches 96$_0$', 96$_1$' comprising encoder network 0' and encoder network 1', respectively, each of which is configured to receive a plurality of concatenated images (respectively images 102$_1$ and images 102$_2$) selected from images 92.

Images 102$_1$ and images 102$_2$ may comprise the same or a different numbers of images and, in either case, may constitute overlapping or non-overlapping sets of images.

Figure 4:
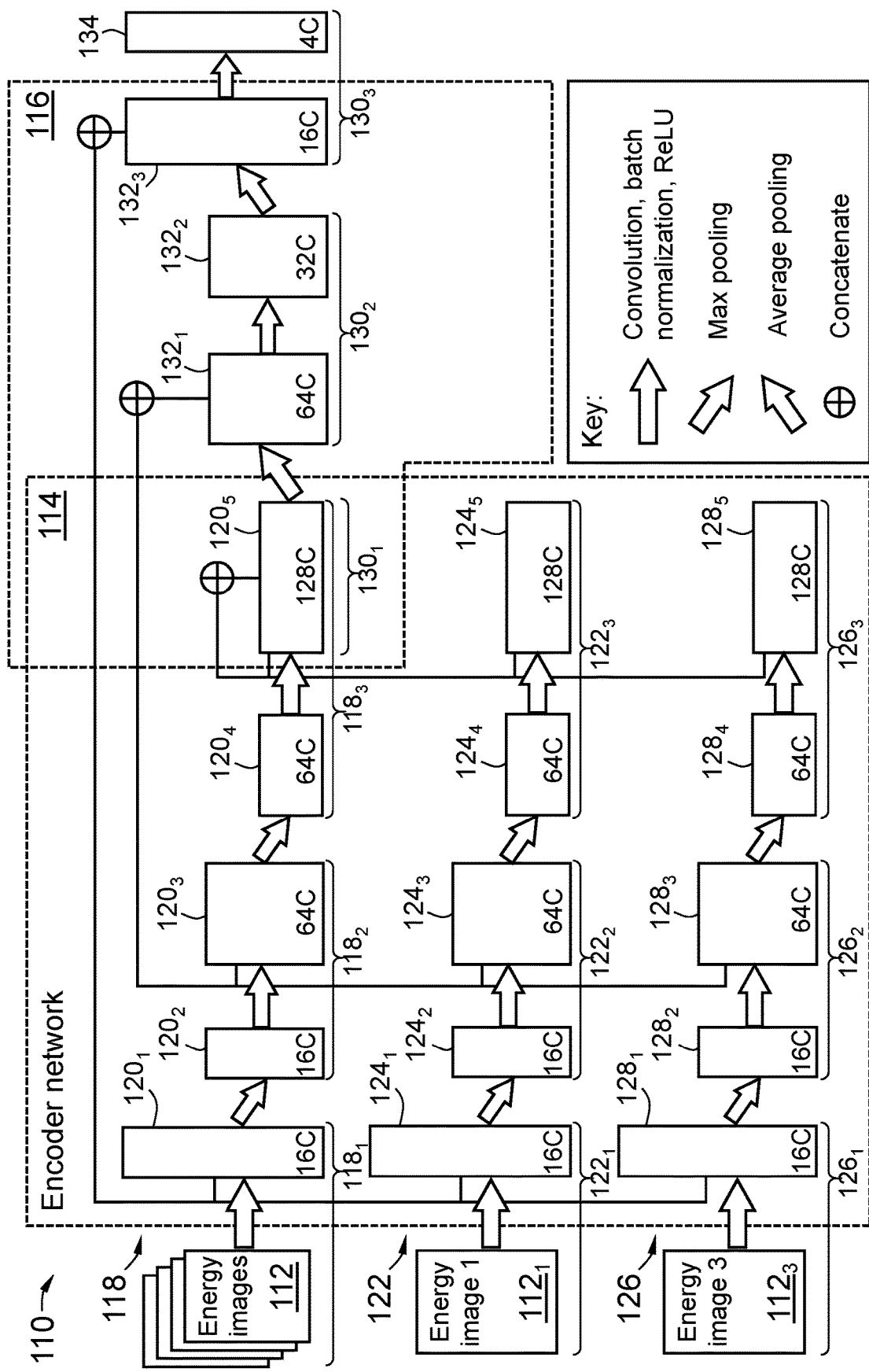
FIG. 4 is a schematic view of a deep learning neural network for generating material decomposition images from plural-energy images according to an embodiment of the present invention.

FIG. 4 is a schematic view of a deep learning neural network 110 (such as may be employed as neural network 42 of system 10), for generating basis material images from plural-energy images according to an embodiment of the present invention. Neural network 110 is shown with input in the form of a plurality (in this example, four) of plural-energy x-ray based images 112.

Neural network 110 includes a multi-branch encoder network 114 and a decoder network 116. In this embodiment, encoder network 114 has a first set of encoder branches comprising a single branch: a first branch 118 that receives the combination of all four images 112 as input. Encoder network 114 has a second set of encoder branches comprising, in this example, two branches: a second branch 122 that receives the first image 112$_1$ (being the first of plural-energy x-ray based images 112) as input, and a third branch 126 that receives the third image 112$_3$ (being the third of plural-energy x-ray based images 112) as input.

The encoder network structure of each of the three encoder branches 118, 122, 126 is identical, each encoder branch containing three stages defined by the size of its feature maps, with each stage containing the convolutions, batch normalization, and ReLU (Rectified Linear Unit) functions or operations. Thus, the first branch 118 comprises a first stage 118$_1$ that includes 16 channel first feature map 120$_1$, which is the same width and height as the original combination of images 112 (which may also be regarded as a part of first stage 118$_1$ of the first branch). The second stage 118$_2$ includes 16 channel second feature map 120$_2$ and 64 channel third feature map 120$_3$, while the third stage 118$_3$ includes 64 channel fourth feature map 120$_4$ and 128 channel fifth feature map 120$_5$.

Likewise, the second branch 122 comprises a first stage 122$_1$ that includes 16 channel first feature map 124$_1$, which is the same width and height as the first individual image 112$_1$ (which may also be regarded as a part of first stage 122$_1$ of the second branch). The second stage 122$_2$ includes 16 channel second feature map 124$_2$ and 64 channel third feature map 124$_3$, while the third stage 122$_3$ includes 64 channel fourth feature map 124$_4$ and 128 channel fifth feature map 124$_5$.

The third branch 126 comprises a first stage 126$_1$ that includes 16 channel first feature map 128$_1$, which is the same width and height as third individual image 112$_3$ (which may also be regarded as a part of the first stage 126$_1$ of the third branch). The second stage 126$_2$ includes 16 channel second feature map 128$_2$ and 64 channel third feature map 128$_3$, while the third stage 126$_3$ includes 64 channel fourth feature map 128$_4$ and 128 channel fifth feature map 128$_5$. The feature map 120$_1$, 124$_1$, 128$_1$ of each respective first stage 118$_1$, 122$_1$, 126$_1$, and the last feature map 120$_3$, 124$_3$, 128$_3$ of each respective second stage 118$_2$, 122$_2$, 126$_3$ undergoes max pooling, reducing the size of the feature maps and allowing encoder network 114 to find the global features of the respective input images 112, 112$_1$, 112$_3$. (Note that the pooling operation is on the feature representations or maps between two stages, which is why there are two pooling operations for the three stages.)

In this embodiment, decoder network 116 also contains three stages, with the last feature map 120$_5$ of the first stage of decoder network 114 also acting as the first stage of encoder network 116. Each of the three stages 130$_1$, 130$_2$, 130$_3$ of decoder network 116 is defined by the size of its respective feature maps: first stage 130$_1$ includes 128 channel feature map 120$_5$, second stage 130$_2$ includes 64 channel feature map 132$_1$ and 32 channel feature map 132$_2$, and third stage 130$_3$ includes 16 channel feature map 132$_3$ and 4 channel feature map 134 (the latter being the outputted basis material image(s)). Each of these three stages 130$_1$, 130$_2$, 130$_3$ contains convolutions, batch normalization, and ReLU operations, and the feature maps of stages 130$_1$, 130$_2$, 130$_3$ undergo average pooling (i.e. a pooling operation is applied to the feature maps between stages 130$_1$ and 130$_2$, and between stages 130$_2$ and 130$_3$), bringing the feature map dimensions back to match those of input images 112, 112$_1$, 112$_3$.

In this embodiment, the feature maps of each stage of the three branches 118, 122, 126 of encoder network 114 are concatenated (hence, respectively, feature maps 120$_1$, 124$_1$, 128$_1$; feature maps 120$_3$, 124$_3$, 128$_3$; and feature maps 120$_5$, 124$_5$, 128$_5$), and then concatenated with the feature maps at the corresponding stage of decoder network 116 (hence, respectively, feature maps 120$_5$, 132$_1$ and 130$_3$). The connection at the multiple levels between multi-branch encoder network 114 and decoder 116 enables neural network 110 to learn the local details of input images 112, 112$_1$, 112$_3$.

Figure 5:
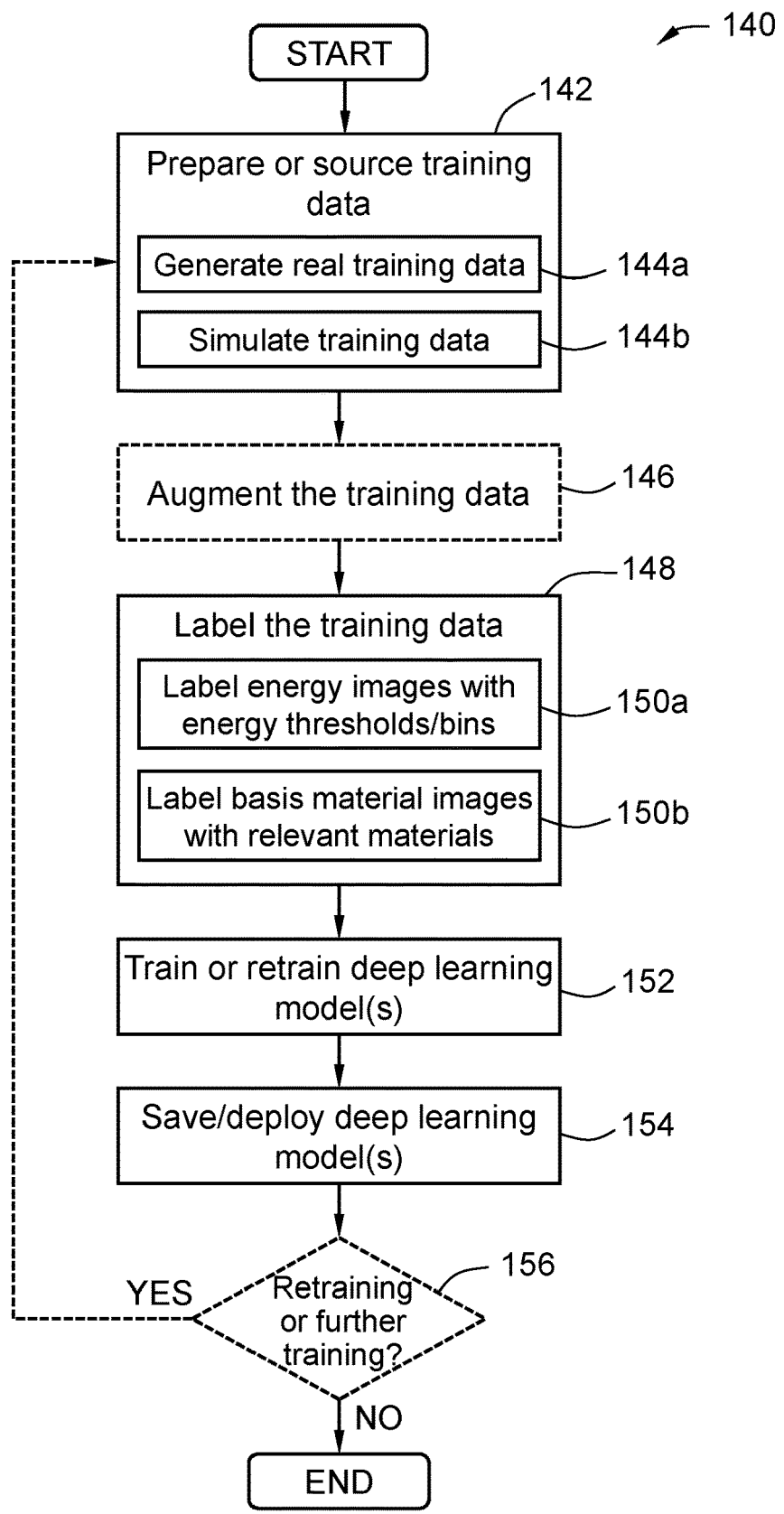
FIG. 5 is a schematic view of the training of the deep learning model or models by the deep learning model trainer of the system of FIG. 1.

FIG. 5 is a flow diagram 140 of the training—by deep learning model trainer 40—of the deep learning model or models stored ultimately in deep learning model(s) 58. At step 142, training data are prepared or sourced, the training data comprising plural-energy x-ray based images and basis material images. The training data may be real data, simulated data, or combinations thereof. In one example, the training data is generated using phantoms of different known materials. In another example, the training data is simulated based on the known characteristics of known materials under different x-ray energies. In some examples, the training data comprises real data only or simulated data only. In another example, the training data comprises some real data and some simulated data. Hence, preparing the training data may involve—for example—generating (or sourcing) real training data (see step 144a) and/or simulating (or sourcing simulated) training data (see step 144b).

The process optionally includes step 146, where the training data is increased using a data augmentation method. This may entail the addition of Gaussian noise to the training data to improve the robustness of the model training, and/or dividing the training data into patches to increase the quantity of training data.

At step 148, the training data are labelled with the appropriate, correct labels. Each 'energy image' (that is, an individual image corresponding to a single energy threshold or energy bin) is labelled with the relevant energy threshold or energy bin (see step 150a), and each basis material image is labelled with the relevant material (see step 150b). At step 152, deep learning model trainer 40 trains one or more deep learning models, employing the correctly labelled energy images and basis material images. Step 152 may entail updating (or retraining) one or more trained deep learning models, if such models have previously been trained and the training data prepared or sourced at step 142 is new or additional training data.

At step 154, the trained or retrained model or models are deployed for use, by being stored in machine learning model(s) 58. Processing then ends, unless the process includes optional step 156 at which deep learning model trainer 40 determines whether retraining or further training is to be conducted. If not, processing ends, but if deep learning model trainer 40 determines that retraining or further training is to be conducted, processing returns to step 142.

In use, system 10 inputs one or more plural-energy x-ray based images into one or more of the now trained deep learning models 58, which process the images and outputs a set of basis material images.

Figure 6A:
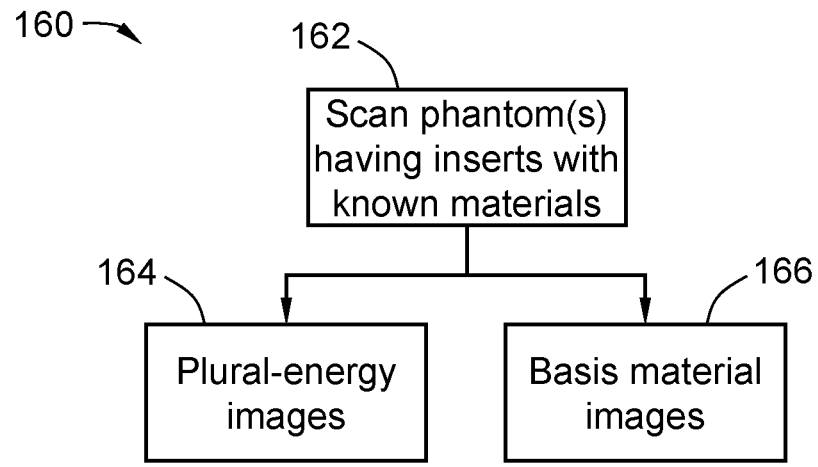
FIGS. 6A and 6B are schematic views of the preparation of exemplary training data.
Figure 6B:
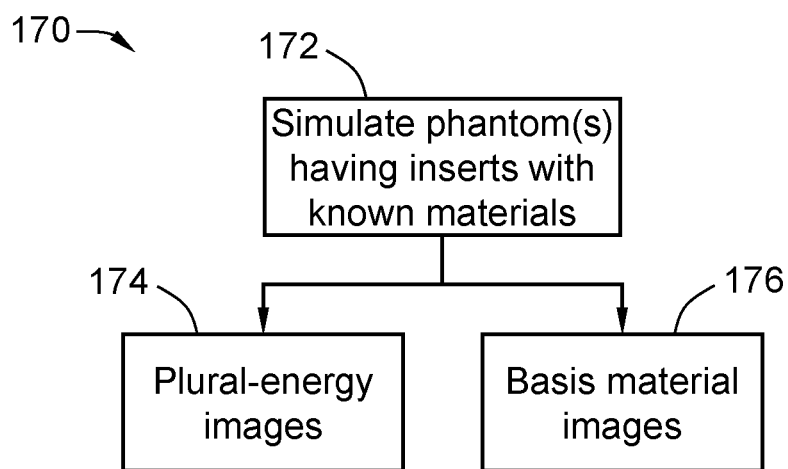

FIGS. 6A and 6B are schematic views of exemplary training data preparation techniques. FIG. 6A shows the preparation 160 of training data using real data. For example, one or more phantoms are used, each having an insert that contains a known material (e.g. HA (hydroxyapatite), iodine, calcium, blood or fat) or a mixture (e.g. iodine and blood) of some or all of the known materials.

The composition, concentration, size and location of each material insert are known. The phantom is scanned 162 using, for example, cold cathode x-ray radiography, dual-energy CT, multi-energy CT or photon-counting CT, such that the plural-energy images are generated 164 with two or more energy thresholds or energy bins. In this example, the aim is to generate three basis material-specific images: a HA image, an iodine image and a fat image. Each basis material-specific image is thus generated 166 with the known concentration, size and location of each material insert.

FIG. 6B shows the preparation 170 of training data using simulated data. For example, one or more phantoms are simulated 172, again with inserts containing known materials (e.g., iodine, calcium, blood, and fat) and a mixture of some of the known materials. The concentration, size and location of each material insert are known. The plural-energy images are simulated 174 based on the known materials and specific energies, such as by creating those images by referring to the real scans, acquired by a plural-energy or photon-counting CT, etc., but with a different concentration of the material. For example, real scans may be acquired by scanning a real phantom with inserts comprising iodine with respective iodine concentrations of 2, 8 and 16 mg/cc using a photon-counting CT. Simulated scans of 20, 25, 30 mg/cc iodine inserts can then be generated by applying a linear fitting to the CT numbers of the real scans, as photon-counting CT maintains a strong linear relationship between CT numbers and the concentrations of the same material. In another example, the energy images are created by mathematical simulation based on the known reaction of known material under different x-ray energies. The basis material-specific images are simulated 176 with the concentration, size and location of each material insert.

Figure 7:
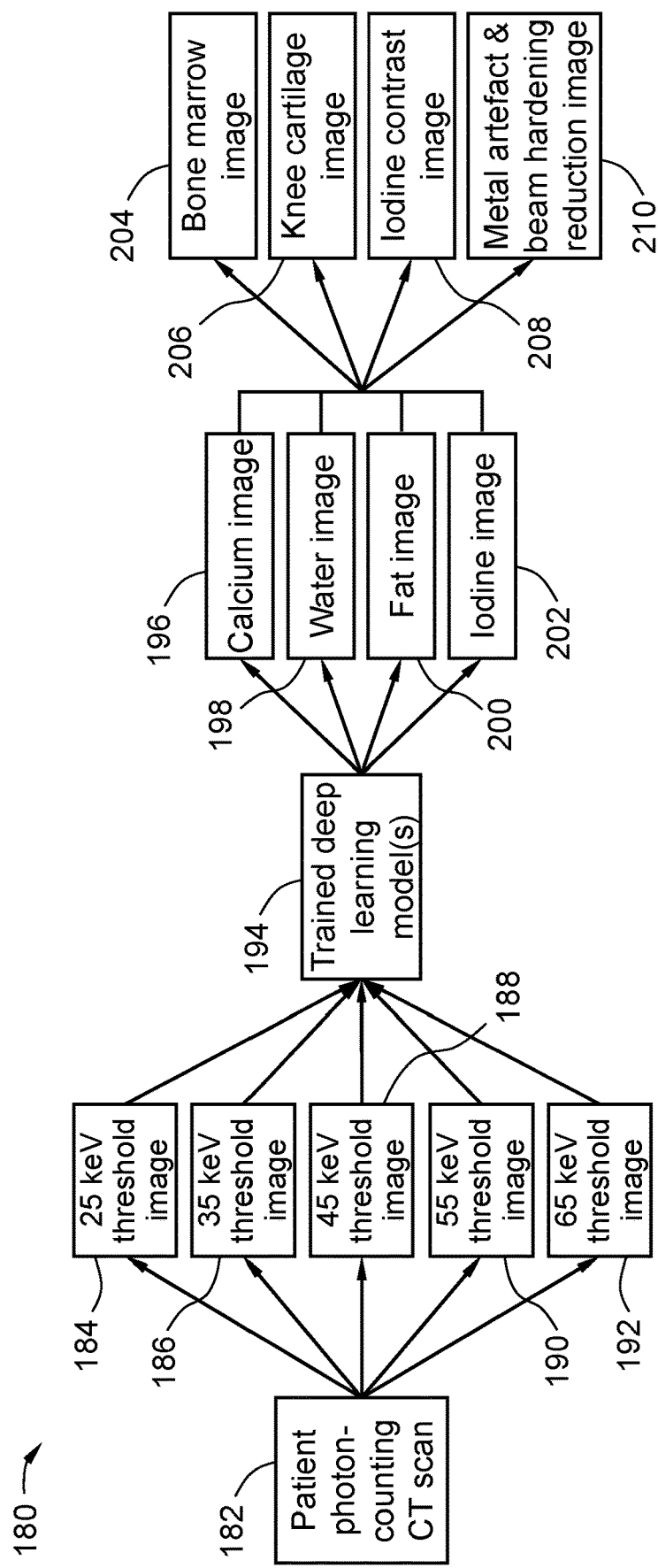
FIG. 7 illustrates an exemplary operation of the system of FIG. 1.

FIG. 7 illustrates an exemplary work flow 180 of system 10 of FIG. 1, for the particular case of a patient that has been injected with an iodine contrast agent then scanned 182 using photon-counting CT. Five images are generated using respectively the five energy thresholds (that is, the energies above which x-rays are counted in the five corresponding energy bins), thereby producing a 25 keV threshold image 184, a 35 keV threshold image 186, a 45 keV threshold image 188, a 55 keV threshold image 190 and a 65 keV threshold image 192. From these images 184, 186, 188, 190, 192, the trained deep learning model or models generate 194 four basis material images: a calcium image 196, a water image 198, a fat image 200 and an iodine image 202. From different linear combinations of the basis material images 196, 198, 200, 202, various functional images are generated for disease diagnostic/monitoring and/or other tasks. For example:

i) a bone marrow image 204 may be generated for bone marrow related disease diagnostic/monitoring (using, for example, HA (hydroxyapatite)+Fat+Water+soft tissue as basis materials/images);

ii) a knee cartilage image 206 may be generated for osteoarthritis or rheumatoid arthritis diagnostic/monitoring (using, for example, HA+Fat+Water+soft tissue as basis materials/images);

iii) an iodine contrast image 208 may be generated for tumor diagnostic/monitoring (using, for example, HA+Fat+Water+soft issue+iodine as basis materials/images); and iv) a metal artefact and beam hardening reduction image 210 may be generated for better image quality (using, for example, HA+soft tissue as basis materials/images).

It will be understood by persons skilled in the art of the invention that many modifications may be made without departing from the scope of the invention. In particular it will be apparent that certain features of embodiments of the invention can be employed to form further embodiments.

It is to be understood that, if any prior art is referred to herein, such reference does not constitute an admission that the prior art forms a part of the common general knowledge in the art in any country.

In the claims that follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

The invention claimed is:

1. A method for generating material decomposition images from a plurality of images obtained with plural-energy x-ray based imaging, the plurality of images corresponding to respective energies of the plural-energy x-ray based imaging, the method comprising:

modelling spatial relationships and spectral relationships among the plurality of images by learning features from the plurality of images in combination and one or more of the plurality of images individually with a deep learning neural network;

generating one or more basis material images employing the spatial relationships and the spectral relationships; and generating one or more material specific or material decomposition images from the basis material images;

wherein the neural network has an encoder-decoder structure and includes a plurality of encoder branches;

each of one or more of the plurality of encoder branches encodes two or more images of the plurality of images in combination; and each of one or more of the plurality of encoder branches encodes a respective individual image of the plurality of images.

2. The method as claimed in claim 1, wherein:
i) each of two or more of the encoder branches encodes a respective different individual image of the plurality of images as input; and/or
ii) a first encoder branch encodes a first combination of two or more images of the plurality of images and a second encoder branch encodes a second combination of two or more images of the plurality of images, wherein the first combination is different from the second combination.

3. The method as claimed either in claim 1, wherein the plural-energy x-ray based imaging comprises cold cathode x-ray radiography, dual-energy radiography, multi-energy radiography, photon-counting radiography, cold cathode x-ray CT, dual-energy CT, multi-energy CT or photon-counting CT.

4. The method as claimed in claim 1, wherein:
a) the encoder branches that encode a respective individual image receive in total all of the images that are received in total by the encoder branches that encode two or more images; or
b) the encoder branches that encode a respective individual image encode in total fewer images than are encoded in total by the encoder branches that encode two or more images; or
c) the encoder branches that encode a respective individual image encode in total more images than are encoded in total by the encoder branches that encode two or more images.

5. The method as claimed in claim 1, wherein the deep learning neural network is a trained neural network, trained with real or simulated training images obtained with real or simulated plural-energy x-ray based imaging and with basis material images.

6. The method as claimed in claim 5, wherein the basis material images comprise any one or more (i) hydroxyapatite images, (ii) calcium images, (iii) water images, (vi) fat images, (v) iodine images, and (vi) muscle images.

7. The method as claimed in claim 1, comprising generating any one or more of (i) a bone marrow decomposition image, (ii) a knee cartilage decomposition image, (iii) an iodine contrast decomposition image, (iv) a tumor decomposition image, (v) a muscle and fat decomposition image, (vi) a metal artefact reduction image, and (vii) a beam hardening reduction image.

8. The method as claimed in claim 1, comprising
generating one or more bone marrow images, and diagnosing, identifying or monitoring bone marrow related disease using the one or more bone marrow images;
generating one or more knee cartilage images, and diagnosing, identifying or monitoring osteoarthritis or rheumatoid arthritis using the one or more bone marrow images;
generating one or more iodine contrast image, and diagnosing, identifying or monitoring a tumor; and/or
generating one or more muscle images, and diagnosing, identifying or monitoring sarcopenia.

9. The method as claimed in claim 1, comprising
generating any one or more (a) bone marrow images, (b) knee cartilage images, (c) iodine contrast images, and (d) muscle images;
generating one or more metal artefact images and/or one or more beam hardening reduction images; and
improving image quality of the bone marrow, knee cartilage, iodine contrast and/or muscle images using the metal artefact and/or beam hardening reduction images.

10. A system for generating material decomposition images from a plurality of images obtained with plural-energy x-ray based imaging, the plurality of images corresponding to respective energies of the plural-energy x-ray based imaging, the system comprising:
a neural network that has an encoder-decoder structure and includes a plurality of encoder branches;
wherein each of one or more of the plurality of encoder branches is configured to encode two or more images of the plurality of images in combination; and
each of one or more of the plurality of encoder branches is configured to encode a respective individual image of the plurality of images;
the neural network is configured to model spatial relationships and spectral relationships among the plurality of images by learning features from the plurality of images in combination and one or more of the plurality of images individually, and to generate one or more basis material images employing the spatial relationships and the spectral relationships; and
the system is configured to generate one or more material specific or material decomposition images from the basis material images.

11. The system as claimed in claim 10, wherein:
i) each of two or more of the encoder branches is configured to encode a respective different image of the plurality of images; and/or
ii) a first encoder branch is configured to encode a first combination of two or more images of the plurality of images and a second encoder branch is configured to encode a second combination of two or more images of the plurality of images, wherein the first combination is different from the second combination.

12. The system as claimed in claim 10, wherein the plural-energy x-ray based imaging comprises cold cathode x-ray radiography, dual-energy radiography, multi-energy radiography, photon-counting radiography, cold cathode x-ray CT, dual-energy CT, multi-energy CT or photon-counting CT.

13. The system as claimed in claim 10, wherein:
a) the encoder branches configured to encode a respective individual image encode in total all of the images that are encoded in total by the encoder branches configured to encode two or more images; or
b) the encoder branches that encode a respective individual image are configured to encode in total fewer images than are encoded in total by the encoder branches that encode two or more images;
or
c) the encoder branches that encode a respective individual image are configured to encode in total more images than are encoded in total by the encoder branches that encode two or more images.

14. The system as claimed in claim 10, wherein the deep learning neural network is a trained neural network, trained with real or simulated training images obtained with real or simulated plural-energy x-ray based imaging and with basis material images.

15. The system as claimed in claim 14, wherein the basis material images comprise any one or more (i) hydroxyapatite images, (ii) calcium images, (iii) water images, (vi) fat images, (v) iodine images, and (iv) muscle images.

16. The system as claimed in claim 10, configured to generate any one or more of (i) a bone marrow decomposition image, (ii) a knee cartilage decomposition image, (iii) an iodine contrast decomposition image, (iv) a tumor decomposition image, (v) a muscle and fat decomposition image, (vi) a metal artefact reduction image, and (vii) a beam hardening reduction image.

17. The system as claimed in claim 10, configured
to generate one or more bone marrow images, and to diagnose, identify or monitor bone marrow related disease using the one or more bone marrow images;
to generate one or more knee cartilage images, and to diagnose, identify or monitor osteoarthritis or rheumatoid arthritis using the one or more bone marrow images;
to generate one or more iodine contrast image, and to diagnose, identify or monitor a tumor; and/or
to generate one or more muscle images, and to diagnose, identify or monitor sarcopenia.

18. The system as claimed in claim 10, configured to generate any one or more (a) bone marrow images, (b) knee cartilage images, (c) iodine contrast images, and (d) muscle images;
generate one or more metal artefact images and/or one or more beam hardening reduction images; and
improve image quality of the bone marrow, knee cartilage, iodine contrast and/or muscle images using the metal artefact and/or beam hardening reduction images.

19. A material decomposition image, generated according to a method for generating material decomposition images from a plurality of images obtained with plural-energy x-ray based imaging, the plurality of images corresponding to respective energies of the plural-energy x-ray based imaging, the method comprising:
modelling spatial relationships and spectral relationships among the plurality of images by learning features from the plurality of images in combination and one or more of the plurality of images individually with a deep learning neural network;
generating one or more basis material images employing the spatial relationships and the spectral relationships; and
generating one or more material specific or material decomposition images from the basis material images;
wherein the neural network has an encoder-decoder structure and includes a plurality of encoder branches;
each of one or more of the plurality of encoder branches encodes two or more images of the plurality of images in combination; and
each of one or more of the plurality of encoder branches encodes a respective individual image of the plurality of images.

20. A non-transient computer-readable medium, comprising a computer program comprising program code configured, when executed by one of more computing devices, to implement a method for generating material decomposition images from a plurality of images obtained with plural-energy x-ray based imaging, the plurality of images corresponding to respective energies of the plural-energy x-ray based imaging, the method comprising:
modelling spatial relationships and spectral relationships among the plurality of images by learning features from the plurality of images in combination and one or more of the plurality of images individually with a deep learning neural network;
generating one or more basis material images employing the spatial relationships and the spectral relationships; and
generating one or more material specific or material decomposition images from the basis material images;
wherein the neural network has an encoder-decoder structure and includes a plurality of encoder branches;
each of one or more of the plurality of encoder branches encodes two or more images of the plurality of images in combination; and
each of one or more of the plurality of encoder branches encodes a respective individual image of the plurality of images.

* * * * *